(12) United States Patent
Desai et al.

(10) Patent No.: US 8,026,275 B2
(45) Date of Patent: Sep. 27, 2011

(54) COMPOSITIONS, METHODS OF USE AND PREPARATION OF 2,6-DIISOPROPYL PHENOL AND ANALOGS FOR ISCHEMIC INJURY

(75) Inventors: Neil P. Desai, Los Angeles, CA (US); Chunlin Tao, Los Angeles, CA (US); Cheng Zhi Yu, San Diego, CA (US); Vuong Trieu, Calabasas, CA (US); Patrick Soon-Shiong, Los Angeles, CA (US)

(73) Assignee: Abraxis BioScience, LLC, Los Angeles, CA (US)

( * ) Notice: Subject to any disclaimer, the term of this patent is extended or adjusted under 35 U.S.C. 154(b) by 402 days.

(21) Appl. No.: 11/816,311

(22) PCT Filed: Feb. 17, 2006

(86) PCT No.: PCT/US2006/005653
§ 371 (c)(1),
(2), (4) Date: Jan. 21, 2009

(87) PCT Pub. No.: WO2006/089120
PCT Pub. Date: Aug. 24, 2006

(65) Prior Publication Data
US 2010/0160448 A1   Jun. 24, 2010

Related U.S. Application Data

(60) Provisional application No. 60/654,146, filed on Feb. 18, 2005.

(51) Int. Cl.
*A01N 43/06* (2006.01)
*A01N 36/00* (2006.01)
*A61K 31/12* (2006.01)
*A61K 31/38* (2006.01)

(52) U.S. Cl. ......... 514/438; 514/675; 514/687; 514/690

(58) Field of Classification Search .................. 514/438, 514/675, 687, 690
See application file for complete search history.

(56) References Cited

U.S. PATENT DOCUMENTS

| | | | |
|---|---|---|---|
| 5,308,874 | A | 5/1994 | Sanchez et al. |
| 5,461,080 | A | 10/1995 | Sanchez et al. |
| 5,714,520 | A | 2/1998 | Jones et al. |
| 5,916,596 | A | 6/1999 | Desai et al. |
| 6,506,405 | B1 | 1/2003 | Desai et al. |
| 6,537,579 | B1 | 3/2003 | Desai et al. |
| 7,586,008 | B2 * | 9/2009 | Tao et al. ............... 568/325 |
| 2005/0004002 | A1 | 1/2005 | Desai et al. |

FOREIGN PATENT DOCUMENTS

| | | | |
|---|---|---|---|
| WO | WO 99/58555 | A2 | 11/1999 |
| WO | WO 2004/033424 | A1 | 4/2004 |
| WO | WO 2004/1009350 | A2 | 11/2004 |
| WO | WO 2005/063665 | A1 | 7/2005 |
| WO | WO 2006/089120 | A3 | 8/2006 |

OTHER PUBLICATIONS

Kohnle (www.med.nyu.edu/patientcare/libray/article.html?ChunkIID) 3 pages (2010).*
Ancrod Stroke Study Investigators, *Stroke*, 25 (9), 1755-1759 (Sep. 1994).
Bayona et al., *Anesthesiology*, 100, 1151-1159 (2004).
Bell et al., *Stroke*, 22 (1), 80-83 (1991).
Blayney et al., *British Dental J.*, 194 (8), 443 (Apr. 26, 2003).
Cooke et al., *Bioorganic & Medicinal Chemistry Letters*, 11, 927-930 (2001).
del Zoppo et al., *Seminars in Neurology*, 11 (4), 368-384 (Dec. 1991).
Delcker et al., *Stroke*, 26, 2016-2022 (1995).
Ergün et al., *Neurosurg. Rev.*, 25, 95-98 (2002).
Gelb et al., *Anesthesiology*, 96, 1183-1190 (2002).
Hacke et al., *Stroke*, 26, 167 (1995).
Jevtovic-Todorovic et al., *Brain Research*, 913, 185-189 (2001).
Kaste et al., *Stroke*, 25 (7), 1348-1353 (Jul. 1994).
Kelly et al., *J. Neurosurg.*, 90, 1042-1052 (1999).
Kinouchi et al., *Proc. Natl. Acad. Sci. USA*, 88, 11158-11162 (Dec. 1991).
Krasowski et al., *J. Pharmacology and Experimental Therapeutics*, 297, 338-351 (2001).
Olney et al., *Science*, 254, 1515-1518 (Dec. 6, 1991).
Peng et al., *Chinese Med. J.*, 116 (5), 731-735 (2003).
Rees et al., *Annual Reports in Medicinal Chemistry*, 31, 41-50 (1996).
Rigobello et al., *Free Radical Research*, 38 (3), 315-321 (Mar. 2004).
Rossetti et al., *Epilepsia*, 45 (7), 757-763 (2004).
Sagara et al., *J. Neurochemistry*, 73 (6), 2524-2530 (1999).
Stadtman, Earl R., *Science*, 257, 1220-1224 (Aug. 28, 1992).
Trapani et al., *J. Med. Chem.*, 41, 1846-1854. (1998).
Trapani et al., *Curr. Med. Chem.*, 7, 249-271 (2000).
Wang et al, *Eur. J. Pharmacology*, 452, 303-308 (2002).
Xia et al., *Cardiovascular Res.*, 59, 113-121 (2003).
Zimmermann, Jerry J., *Chest*, 100 (3), 189S-192S (Sep, 1991).

* cited by examiner

*Primary Examiner* — Brandon Fetterolf
*Assistant Examiner* — Shirley V Gembeh
(74) *Attorney, Agent, or Firm* — Leydig, Voit & Mayer, Ltd.

(57) ABSTRACT

The present invention provides novel 2,6-diisopropyl phenol 2,6-diisopropyl phenol analogs and sterile, stable pharmaceutical compositions of 2,6-diisopropyl phenol 2,6-diisopropyl phenol and analogs thereof useful as an antioxidant in the treatment of ischemic injury including stroke and other cerebral injury. 2,6-diisopropyl phenol or its analogs are administered in a dosage effective to produce blood levels and brain levels of the drug that can prevent free radical damage associated with ischemic injury.

23 Claims, 3 Drawing Sheets

COMPOSITIONS, METHODS OF USE AND PREPARATION OF 2,6-DIISOPROPYL PHENOL AND ANALOGS FOR ISCHEMIC INJURY

CROSS-REFERENCE TO RELATED APPLICATIONS

This patent application claims the benefit of U.S. Provisional Patent Application No. 60/654,146, filed Feb. 18, 2005.

FIELD OF THE INVENTION

The present invention relates to pharmaceutical compositions useful for the treatment and prevention of ischemic injury. In particular, the invention relates to pharmaceutical compositions of 2,6-diisopropyl phenol and analogs, which act as antioxidants and free radical scavengers for the treatment of stroke and other cerebral injury and prevention of resulting reperfusion injury.

BACKGROUND OF THE INVENTION

Stroke is a cardiovascular disease affecting the blood vessels supplying blood to the brain. There are four main types of stroke: two caused by blood clots or other particles, and two by hemorrhage. By far the most common causes for strokes are cerebral thrombosis and cerebral embolism, which are caused by clots or particles that plug an artery. The remaining two are cerebral and subarachnoid hemorrhages caused by ruptured blood vessels.

Stroke is the third leading cause of death in the United States. It kills more than 150,000 people annually and accounts for about one of every 15 U.S. deaths. Stroke is a major source of disability in the developed countries and regions. Typically, ischemic damage, i.e., a lack of oxygen, due to a disruption of the blood supply to a region in the brain is diagnosed as a stroke when accompanied by neurological or other symptoms. In an ischemic stroke, focal ischemia exhibiting a defined region of tissue damage is observed, which is often surrounded by a penumbral region that is susceptible to additional damage over time. When blood supply to the brain is reduced below a critical threshold, a cascade of biochemical events leads to irreversible damage to neurons and brain infarction. Research on treatment and prevention of ischemia is extensive but unfortunately it remains at a basic stage and no adequate therapies are yet in practice.

Stroke is defined as a sudden impairment of body functions caused by a disruption in, e.g., the supply of blood to the brain. For instance, a stroke occurs when a blood vessel bringing oxygen and nutrients to the brain is interrupted by any method including low blood pressure, clogging by atherosclerotic plaque, a blood clot, or some other particle, or when a blood vessel bursts. Because of the blockage or rupture, part of the brain fails to get the blood flow that it requires. Brain tissue that receives an inadequate supply of blood is said to be ischemic. Deprived of oxygen and nutrients, nerve cells and other cell types within the brain begin to fail, creating an infarct (an area of cell death, or necrosis). As nerve cells (neurons) fail and die, the part of the body controlled by those neurons cannot function either. The devastating effects of ischemia are often permanent because brain tissue has very limited repair capabilities and lost neurons are not usually replaced. The blood supply disruption resulting in a stroke may be due to, inter alia, presence of a blood clot, arteriosclerosis, artherosclerotic plaque (or its components), and the like. Thus, treatment for a stroke has to be, preferably, provided rapidly to avoid irreversible damage. The treatment also has to be in agreement with the underlying cause because, for instance, administering agents to inhibit blood coagulation in a stroke due to a hemorrhage risks increasing the damage by promoting hemorrhage. If the stroke is due to the presence or formation of a blood clot, then treatments are directed to dissolve or otherwise reduce the clots.

Cerebral ischemia may be incomplete (blood flow is reduced but not entirely cut off), complete (total loss of tissue perfusion), transient or permanent. If ischemia is incomplete and persists for no more than ten to fifteen minutes, neural death might not occur. More prolonged or complete ischemia results in infarction. Depending on the site and extent of the infarction, mild to severe neurological disability or death will follow. Thus, the chain of causality leading to neurological deficit in stroke has two principal components: loss of blood supply, and cell damage and death.

Thrombosis is the blockage of an artery by a large deposit that usually results from the combination of atherosclerosis and blood clotting. Thrombotic stroke (also called cerebral thrombosis) results when a deposit in a brain or neck artery reaches occlusive proportions. Most strokes are of this type.

Embolism is the blockage of an artery or vein by an embolus. Emboli are often small pieces of blood clot that break off from larger clots. Embolic stroke (also called cerebral embolism) occurs when an embolus is carried in the bloodstream to a brain or neck artery. If the embolus reaches an artery that is too small for it to pass through, it plugs the artery and cuts off the blood supply to downstream tissues. Embolic stroke is the clinical expression of this event.

Once deprived of blood, and, hence oxygen and glucose, brain tissue may undergo ischemic necrosis or infarction. The metabolic events thought to underlie such cell degeneration and death include: energy failure through ATP depletion; cellular acidosis; glutamate release; calcium ion influx; stimulation of membrane phospholipid degradation and subsequent free-fatty-acid accumulation; and free radical generation.

Knowledge of these underlying events has led investigators studying certain types of ischemic injury to utilize agents such as calcium channel blockers, glutamate and glycine antagonists, CDP-amines, free radical scavengers/antioxidants, perfluorocarbons and thrombolytic agents to improve cerebral blood flow and/or neurological outcome, all with mixed results. Certain calcium-channel blockers have been reported to produce inconsistent results and undesirable side effects, such as reduction in pulse or perfusion pressure. See, e.g., Kaste, M. et al. *Stroke* (1994) 25:1348-1353.

Glutamate antagonists have been observed to reduce infarct size under certain experimental conditions. See, e.g., Olney, J. W. et al. *Science* (1991) 254:1515-1518. However, most, if not all, of these compounds cause brain vacuolization and most produce phencyclidine-like subjective effects in animals and humans. Ingestion of phencyclidine has been associated with euphoria, anxiety, mood lability and prolonged psychosis.

Although perfluorocarbons have shown some benefit in the outcome from ischemic stroke, these compounds have an extremely long half-life and must be infused into the brain and spinal fluid. In addition, these compounds have been observed to cause gonadal hypertrophy. See, Bell, R. D. et al. *Stroke* (1991) 22:80-83.

Thrombolytic agents, such as t-PA (tissue plasminogen activator), streptokinase, and urokinase, have shown some promise in the treatment of ischemia. However, these agents have the propensity to increase intracranial bleeding, which, ultimately, can lead to increased mortality. See, e.g., del Zoppo, G. J. et al. *Seminars in Neurology* (1991) 11(4):368-384; The Ancrod Stroke Study Investigators, *Stroke* (1994) 25:1755-1759; Hacke, W. et al. *Stroke* (1995) 26:167. Moreover, the efficacy of these agents may be limited to treatment within the first three hours of stroke.

Free radical scavengers/antioxidants are a heterogenous group of compounds. In general, the effects of these compounds on infarct volume have been inconsistent. For example, superoxide dismutase inhibitors have been found to reduce infarct volume only when injected intracerebroventricularly. See, Kinouchi, H. et al. *Proc. Natl. Acad. Sci. USA* (1991) 88:11158-11162. Other compounds, such as lubeluzole, have been shown to have clinical benefit but with a very narrow margin of safety. See, Diener, H. C. et al. *Stroke* (1995) 26:30.

Free radicals, particularly free radicals derived from molecular oxygen, are believed to play a fundamental role in a wide variety of biological phenomena. In fact, it has been suggested that much of what is considered critical illness may involve oxygen radical ("oxyradical") pathophysiology (Zimmerman, J. J. (1991) *Chest* 00:1895). Oxyradical injury has been implicated in the pathogenesis of pulmonary oxygen toxicity, adult respiratory distress syndrome (ARDS), bronchopulmonary dysplasia, sepsis syndrome, and a variety of ischemia-reperfusion syndromes, including myocardial infarction, stroke, cardiopulmonary bypass, organ transplantation, necrotizing enterocolitis, acute renal tubular necrosis, and other disease. Oxyradicals can react with proteins, nucleic acids, lipids, and other biological macromolecules producing damage to cells and tissues, particularly in the critically ill patient.

Many free radical reactions are highly damaging to cellular components, i.e., they crosslink proteins, mutagenize DNA, and peroxidize lipids. Once formed, free radicals can interact to produce other free radicals and non-radical oxidants such as singlet oxygen ($^1O_2$) and peroxides. Degradation of some of the products of free radical reactions can also generate potentially damaging chemical species. For example, malondialdehyde is a reaction product of peroxidized lipids that reacts with virtually any amine-containing molecule. Oxygen free radicals also cause oxidative modification of proteins (Stadtman, E. R. (1992) *Science* 257:1220).

In order to prevent the damaging effects of free radicals and free radical-associated diseases, great efforts have been made to develop new antioxidants that are efficient at removing dangerous oxyradicals, particularly superoxide and hydrogen peroxide, and that are inexpensive to manufacture, stable and possess advantageous pharmacokinetic properties, such as the ability to cross the blood-brain barrier and penetrate tissues. Although enhancement of the tolerance of cerebral tissue to ischemia/reperfusion injury has been a goal to complement or replace agents that restore or promote blood flow, clinical trials have so far failed to identify a safe and effective neuroprotectant. Promising neuroprotectant candidates that do not cause unacceptable adverse side effects are almost non-existent. At present, there is no neuroprotectant drug that may be administered by the patient (even with the assistance from relatives) prior to hospital arrival. The reasons include: requirement of intravenous loading dose, adverse effects, narrow therapeutic time window, and potentially serious side effects in patients without stroke or with hemorrhagic stroke. Thus, treating a hemorrhagic stroke with clot fighting agents is likely to seriously exacerbate the damage.

Thus, there is a need for versatile and effective new pharmaceutical compositions comprising antioxidants and free radical scavengers, that limit the extent or otherwise treat nerve cell death (degeneration) such as may occur with ischemic injury.

In addition, while many antioxidant and free radical scavenger compositions are known in the art, a significant limitation of the prior art compositions is their inability to effectively penetrate the blood brain barrier, thus limiting the effectiveness of the prior art compositions in treatment of cerebral ischemic injury.

2,6-diisopropyl phenol (2,6-diisopropylphenol, formula I), is a short-acting hypnotic agent, effective for induction and maintenance of anesthesia (see, e.g., Rees et al., *Annu. Rep. Med. Chem.*, 31, 41-50 (1996), and Trapani et al., *Curr. Med. Chem.*, 7, 249 (2000)). 2,6-diisopropyl phenol also is used for intravenous (IV) sedation by target-controlled infusions (see, e.g., Leitch, *Br. Dent. J.*, 194, 443 (2003)). It is highly lipid-soluble and has a characteristic property that it can readily permeate biomembranes such as blood brain barrier (BBB).

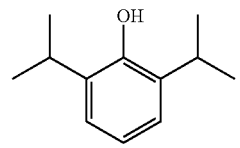

2,6-diisopropyl phenol has been used in the treatment of pathologies relating to the presence of free oxygen radicals (see, e.g., U.S. Pat. Nos. 5,308,874 and 5,461,080). 2,6-diisopropyl phenol has been shown to repair neural damage caused by free oxygen radicals in vitro (see, e.g., Sagara et al., *J. Neurochem.*, 73, 2524 (1999) and Jevtovic-Todorovic et al., *Brain Res.*, 913, 185 (2001)) and has been used in vivo to treat head injury (see, e.g., Kelly et al., *J. of Neurosurgery*, 90, 1042 (1999)). Furthermore, 2,6-diisopropyl phenol is considered an alternative to barbiturates for the management of refactory status epolepticus (Rossetti, et al., 2004, Epilepsia, 45(7): 757-763).

There is evidence suggesting that 2,6-diisopropyl phenol can protect endothelial cells against oxidative stress by inhibiting eNOS transcription and protein expression (see, e.g., Peng et al., *Chin. Med. J.* (Engl)., 116(5), 731-5 (2003)). Moreover, 2,6-diisopropyl phenol enhances ischemic tolerance of middle-aged hearts, primarily by inhibiting lipid peroxidation (see, e.g., Xia et al., *Cardiovasc. Res.*, 59, 113 (2003)).

It has now been found that 2,6-diisopropyl phenol and its analogs act as antioxidants and free radical scavengers, and can effectively penetrate the blood brain barrier. 2,6-diisopropyl phenol and its analogs are thus useful for the treatment or prevention of cellular damage in various tissues from injuries associated with ischemia, and hence they are useful for the treatment or prevention of injuries of reperfusion in acute cerebral infarction due to abnormal generation of active oxygen species.

The invention provides novel 2,6 diisopropyl phenol compositions and analogs with antioxidant or neuroprotective activity effective for the treatment of ischemic injury. Also provided is a method for timely treatment of a sudden onset of at least one neurological deficit in a subject. These and other advantages of the invention, as well as additional inventive features, will be apparent from the description of the invention provided herein.

BRIEF SUMMARY OF THE INVENTION

Figure 1A:
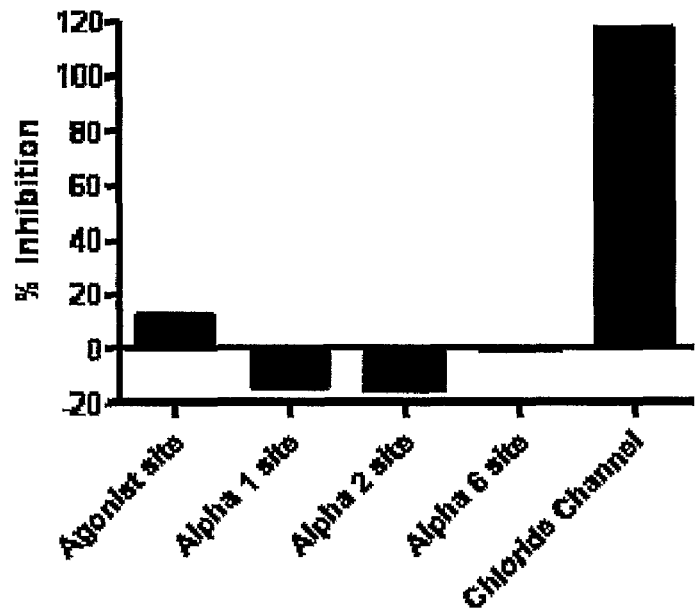
FIG. 1A is a bar chart depicting the effect of 2,6 diisopropyl phenol ($10^{-4}$M) on the percent inhibition of binding of TBOB to various sites of the $GABA_A$ receptor: the chloride chanel, the agonist site, the alpha-1 site, the alpha-2 site, and the alpha-6 site.

The present invention in one of its embodiments provides for sterile, stable pharmaceutical compositions comprising 2,6-diisopropyl phenol, analogs of 2,6-diisopropyl phenol and mixtures of 2,6-diisopropyl phenol and analogs of 2,6-diisopropyl phenol. The compositions of the present invention are suitable for the treatment of stroke and other cerebral injury, and for the prevention of ischemic injury resulting from stroke or other cerebral injury.

The present invention provides pharmaceutical compositions comprising 2,6-diisopropyl phenol or analogs thereof for the treatment of ischemic injury, including, for example, ischemic optic neuropathy, ischemic retinopathy, stroke, reperfusion injury and other cerebral injury.

The present invention provides pharmaceutical compositions comprising 2,6-diisopropyl phenol or analogs thereof for the prevention of ischemic injury, including, for example, ischemic optic neuropathy, ischemic retinopathy, stroke, reperfusion injury and other cerebral injury.

The present invention provides a method of treating ischemic reperfusion injury in a mammal by the administration of pharmaceutical compositions comprising 2,6-diisopropyl phenol or analogs thereof.

The present invention also provides a method of preventing ischemic reperfusion injury in a mammal by the administration of pharmaceutical compositions comprising 2,6-diisopropyl phenol or analogs thereof.

The present invention also provides pharmaceutical compositions comprising 2,6-diisopropyl phenol or analogs thereof for the prevention of the damaging effects of free radicals and free radical-associated diseases.

The present invention further provides methods of using 2,6-diisopropyl phenol or analogs thereof for the treatment of ischemic injury, comprising the administration of 2,6-diisopropyl phenol or analogs to a human in an amount effective for the treatment of ischemic injury, including, for example, ischemic optic neuropathy, ischemic retinopathy, stroke, reperfusion injury and other cerebral injury.

The present invention provides methods of making pharmaceutical compositions comprising 2,6-diisopropyl phenol or analogs thereof for the prevention of ischemic injury, including, for example, ischemic optic neuropathy, ischemic retinopathy, stroke, reperfusion injury and other cerebral injury.

A method of making pharmaceutical compositions comprising 2,6-diisopropyl phenol or analogs thereof for the treatment or prevention of the damaging effects of free radicals and free radical-associated diseases is also provided. A method for timely treatment Of a sudden onset of at least one neurological deficit in a subject is disclosed. The sudden onset of neurological symptoms is an indicator of a possible stroke, also termed a cerebrovascular accident. The method comprises administering an effective amount of 2,6-diisopropyl phenol or analogs thereof to the subject immediately after the sudden onset of the at least one neurological deficit, and preferably the administration of 2,6-diisopropyl phenol or analogs thereof is within three hours of the sudden onset of the at least one neurological deficit.

These and other features and advantages of the present invention will become apparent from the subsequent detailed description of the preferred embodiment and the appended claims.

DETAILED DESCRIPTION OF THE INVENTION

The present invention is predicated on the discovery that 2,6-diisopropyl phenol and its analogs are capable of acting as antioxidants. Prior to the present invention, there has been a need to develop new stable antioxidants capable of crossing the blood-brain barrier and penetrating tissues to prevent the damaging effects of free radicals and free radical-associated diseases. The inventive compounds are useful to treat ischemia due to stroke, hemmorhage, or trauma. In one embodiment, the invention provides methods for the treatment of ischemic injury and ischemic reperfusion injury by the use of 2,6-diisopropyl phenol or 2,6-diisopropyl phenol analogs and prodrugs. In another embodiment, the invention provides stable, parenteral pharmaceutical compositions of 2,6-diisopropyl phenol and its analogs, that are useful for the treatment of cellular damage in tissue from injuries associated with ischemic injury, for the prevention of cellular damage in tissue from injuries associated with ischemic injury or for both prevention and treatment of such cellular damage. Preferably, 2,6-diisopropyl phenol or analogs of 2,6-diisopropyl phenol are administered in an amount effective to produce blood levels and brain levels of the drug to treat or prevent free radical damage associated with ischemic injury. The invention encompasses a method for timely treatment of a sudden onset of at least one neurological deficit in a subject. The sudden onset of neurological symptoms is an indicator of a possible stroke, also termed a cerebrovascular accident. The administration of 2,6-diisopropyl phenol or analogs thereof serves to protect cerebral tissue from ischemia related damage. The method comprises administering an effective amount of 2,6-diisopropyl phenol or analogs thereof to a subject immediately after a sudden onset of at least one neurological deficit.

2,6-diisopropyl phenol and analogs thereof can be formulated into pharmaceutical compositions for administration to a patient, preferably a human patient. Any of a number of suitable pharmaceutical formulations can be utilized as a vehicle for the administration of the compounds of the invention. Preferably, the inventive compounds are formulated for general pharmaceutical use. Most preferably, the inventive compounds and pharmaceutical compositions are formulated for use in ischemic injury, or for the treatment of ischemic reperfusion injury. Particularly preferred are low oil formulations of 2,6-diisopropyl phenol and analogs thereof. Low oil formulations may contain less than 5 wt % oil, preferably less than 3 wt %, preferably less than 2 wt %. Examples of low oil formulations are described in U.S. Patent Application No. 2005-0004002, incorporated herein by reference.

Examples of analogs of 2,6-diisopropyl phenol that cross the blood-brain barrier and that are antioxidants include:

(4-fluorophenyl)-(4-hydroxy-3,5-diisopropylphenyl)methanone, (4-(trifluoromethyl)phenyl)-(4-hydroxy-3,5-diisopropylphenyl)methanone, (4-hydroxy-3,5-diisopropylphenyl)-(4-nitrophenyl)methanone, (3-fluoro-4-(trifluoromethyl)phenyl)-(4-hydroxy-3,5-diisopropylphenyl)methanone, (3-(trifluoromethyl)phenyl)-(4-hydroxy-3,5-diisopropylphenyl)methanone, (3-fluoro-5-(trifluoromethyl)phenyl)-(4-hydroxy-3,5-diisopropylphenyl)methanone, (4-hydroxy-3,5-diisopropylphenyl)-(naphthalen-2-yl)methanone, (3,5-bis(trifluoromethyl)phenyl)-(4-hydroxy-3,5-diisopropylphenyl)methanone, (4-tert-butylphenyl)-(4-hydroxy-3,5-diisopropylphenyl)methanone, (4-hydroxy-3,5-diisopropylphenyl)-(4-isobutylphenyl)methanone, (4-hydroxy-3,5-diisopropylphenyl)-(4-iodophenyl)methanone, (4-hydroxy-3,5-diisopropylphenyl)-(4-methoxyphenyl)methanone, (4-cyanophenyl)-(4-hydroxy-3,5-diisopropylphenyl)methanone, (6-(trifluoromethyl)pyridin-3-yl)-(4-hydroxy-3,5-diisopropylphenyl)methanone, (4-bromophenyl)-(4-hydroxy-3,5-diisopropylphenyl)methanone, (4-hydroxy-3,5-diisopropylphenyl)-(4-propylphenyl)methanone, (4-chlorophenyl)-(4-hydroxy-3,5-diisopropylphenyl)methanone, 4-((4-(trifluoromethyl)phenyl)-(methoxyimino)methyl)-2,6-diisopropylphenol, 4-(4-(trifluoromethyl)benzyl)-2,6-diisopropylphenol, 4-((4-(trifluoromethyl)phenyl)-(hydroxy)methyl)-2,6-diisopropylphenol, and 4-hydroxy-3,5-diisopropylphenyl)-(4-(methylsulfonyl)phenyl)methanone.

Thus, 2,6-diisopropyl phenol and analogs of 2,6-diisopropyl phenol are useful for the treatment or prevention of ischemic injury and ischemic reperfusion injury.

Compositions according to the invention can be administered to a patient by conventional administration methods for anesthetics, such as, for example, oral administration, nasal respiratory administration, bolus injection, intravenous administration by repeated doses or by continuous infusion, intra-arterial administration, sub-lingual administration, parenteral administration, rectal administration, vaginal administration, sublingual administration, cutaneous administration, and slow release routes. Preferably, the pharmaceutical composition is administered by continuous infusion.

The compositions of the invention may be administered by one or more times a day (i.e., 1, 2, 3, 4, or 5 or more times a day) via one or more of the above routes of administration or continuously (i.e., via infusion). The composition may be administered for one or more days as needed. That is, the composition may be administered for 1, 2, 3, 4, 5, or more consecutive days. Further, the composition may be administered for a number of non-consecutive days as needed by the recipient. Dosages administered may be adjusted according to the age, gender, body weight/composition of the recipient as well as according to the characteristics of the composition to be administered. In a preferred embodiment, the composition to be administered comprises 4-(trifluoromethyl)phenyl)-(4-hydroxy-3,5-diisopropylphenyl)methanone.

Typically, 2,6-diisopropyl phenol or an analog of 2,6-diisopropyl phenol is mixed with a carrier, diluted by a carrier, or enclosed within a carrier which can be in the form of a capsule, sachet, paper, or other container. When the carrier serves as a diluent, it can be a solid, semi-solid, or liquid material which acts as a vehicle, excipient, or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments which contain, for example, up to 10% by weight of the active compound, soft and hard gelatin capsules, suppositories, sterile injectable solutions, and sterile packaged powders.

For oral administration, 2,6-diisopropyl phenol or an analog of 2,6-diisopropyl phenol is incorporated into suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone, or gelatin.

Examples of suitable carriers, excipients, and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate, and mineral oil. The formulations can additionally include lubricating agents, wetting agents, emulsifying and suspending agents, preserving agents, sweetening agents or flavoring agents. Examples of emulsifying agents include the Tweens, e.g., Tween™ 80 and related compounds, cremophor and related compounds, tocopherol esters such as tocopheryl polyethylene glycol succinate and like, pluronics, emulsifiers based on polyoxy ethylene compounds, Span™ 80 and related compounds, lecithins, phospholipids artificial and natural and related compounds, and other emulsifiers known in the art and approved for use in animals or human dosage forms. The compositions can be formulated so as to provide rapid, sustained or delayed release of the active ingredient after administration to the patient by employing procedures well known in the art, Preferred compositions for administration by injection include those comprising a novel biologically active analogue as the active ingredient, in association with a surface-active agent (or wetting agent or surfactant), or in the form of an emulsion (e.g., as a water-in-oil or oil-in-water emulsion). Suitable surface-active agents include, in particular, nonionic agents, such as polyoxyethylenesorbitans (e.g., Tween™ 20, 40, 60, 80, or 85), and other sorbitans (e.g., Span™ 20, 40, 60, 80, or 85). Other ingredients can be added, for example, mannitol or other pharmaceutically acceptable vehicles, if necessary.

The 2,6-diisopropyl phenol formulations described in U.S. Pat. No. 5,714,520 is sold as DIPRIVAN® and comprises a sterile, pyrogen-free emulsion containing 1% (w/v) 2,6-diisopropyl phenol in 10% (w/v) soybean oil. The formulation also contains 1.2% (w/v) egg lecithin as a surfactant, 2.25% (w/v) glycerol to make the formulation isotonic, sodium hydroxide to adjust the pH, and EDTA 0.0055% (w/v) as a preservative. This formulation prevents no more than a 10-fold increase against gram negative (such as *Pseudomonas aeruginosa* and *Escherichia coli*) and gram positive (*Staphylococcus aureus*) bacteria, as well as yeast (such as *Candida albicans*) over a twenty-four hour period. However, EDTA, which is a metal ion chelator, removes cations like calcium magnesium and zinc. This can be potentially dangerous to some patients with low calcium or other low cation levels, and especially critical for ICU patients.

The present invention also provides methods for the formation of nanoparticles of 2,6-diisopropyl phenol and its analogs by a solvent evaporation technique from an oil-in-water emulsion prepared under conditions of high shear forces (e.g., sonication, high pressure homogenization, or the like). The preparation of nanoparticles from biocompatible polymers (e.g., albumin) is disclosed in, for example, U.S. Pat. Nos. 5,916,596, 6,506,405, and 6,537,579.

Thus, in accordance with the present invention, 2,6-diisopropyl phenol and analogs of 2,6-diisopropyl phenol can be dissolved in pharmaceutically acceptable solvent or in solvents at a final concentration in the range of about 1-99% v/v, more preferably in the range of about 5-25% v/v. Solvents include, for example, ethyl acetate, ethanol, tetrahydrofuran, dioxane, acetonitrile, acetone, dimethyl sulfoxide, dimethyl formamide, methyl pyrrolidinone, oils such as soybean oil, safflower oil and other injectable oils and the like.

The pharmaceutically acceptable carrier may be a solution, emulsion or suspension. For example, an emulsion of 2,6-diisopropyl phenol in oil, stabilized by lecithin is well known in the art. Such an emulsion may be used for treatment of ischemic injury. Other invention emulsion or nanoparticles formulations may also be prepared. An emulsion is formed by homogenization under high pressure and high shear forces. Such homogenization is conveniently carried out in a high-pressure homogenizer, typically operated at pressures in the range of about 3,000 up to 30,000 psi. Preferably, such processes are carried out at pressures in the range of about 6,000 up to 25,000 psi. The resulting emulsion comprises very small nanodroplets of the nonaqueous solvent containing the dissolved pharmacologically active agent and very small nanodroplets of the protein-stabilizing agent. Acceptable methods of homogenization include processes imparting high shear and cavitation such as, for example, high-pressure homogenization, high shear mixers, sonication, high shear impellers, and the like.

Colloidal systems prepared in accordance with the present invention can be further converted into powder form by removal of the water, e.g., by lyophilization at a suitable temperature-time profile. The protein (e.g., human serum albumin) itself acts as a cryoprotectant, and the powder is easily reconstituted by addition of water, saline or buffer, without the need to use conventional cryoprotectants such as mannitol, sucrose, glycine, and the like. While not required, it is of course understood that conventional cryoprotectants can be added to the pharmaceutical compositions if so desired.

In one embodiment of the invention, nanoparticles of the inventive compounds can be administered by any acceptable route including, but not limited to, orally, intramuscularly, transdermally, intravenously, through an inhaler or other air borne delivery systems, and the like. When preparing the composition for injection, particularly for intravenous delivery, the continuous phase preferably comprises an aqueous solution of tonicity modifiers, buffered to a pH below 7, more preferably below 6.

The nanoparticles of this invention can be enclosed in a hard or soft capsule, can be compressed into tablets, or can be incorporated with beverages, food, or otherwise incorporated into the diet. Capsules can be formulated by mixing the nanoparticle with an inert pharmaceutical diluent and inserting the mixture into a hard gelatin capsule of the appropriate size. If soft capsules are desired, a slurry of the compound with an acceptable vegetable oil, light petroleum, or other inert oil can be encapsulated by machine into a gelatin capsule.

Those skilled in the art will recognize that several variations are possible within the scope and spirit of this invention. The following examples further illustrate the invention but, of course, should not be construed as in any way limiting its scope.

EXAMPLE 1

Preparation of 2,6-diisopropyl phenol Nanoparticles

This example demonstrates the preparation of a pharmaceutical composition containing 1% oil and comprising 2,6-diisopropyl phenol and albumin. An oil-in-water emulsion containing 2% (by weight) of 2,6-diisopropyl phenol was prepared as follows. The aqueous phase was prepared by adding glycerol (2.25% by weight) and human serum albumin (0.5% by weight) into water for injection and stirred until dissolved. The aqueous phase was passed through a filter (0.2 μm filter). The oil phase was prepared by dissolving egg lecithin (0.4% by weight) and 2,6-diisopropyl phenol (2% by weight) into soybean oil (1% by weight) at about 50-60° C. and was stirred until dissolved. The oil phase was added to the aqueous phase and homogenized at 10,000 RPM for 5 min. The crude emulsion was high pressure homogenized at 20,000 psi and recirculated for 15 cycles at 5° C. Alternately, discrete passes through the homogenizer were used. The final emulsion was filtered (0.2 μm filter) and stored under nitrogen. The resulting pharmaceutical composition contained the following general ranges of components (weight %): 2,6-diisopropyl phenol 0.5-5%; human serum albumin 0.5-3%; soybean oil 0.5-3.0%; egg lecithin 0.05-1.2%; glycerol 2.25%; water for injection q.s. to 100; pH 5-8. Suitable chelators, e.g., deferoxamine (0.001-0.1%), were optionally added.

EXAMPLE 2

Preparation of (4-fluorophenyl)-(4-hydroxy-3,5-diisopropylphenyl)methanone (1)

To a solution of 2,6-diisopropylphenol (3.3 g, 18.5 mmol) in 98 mL of toluene were added dropwise 4-fluorobenzoyl chlroride (4 mL, 37 mmol) and aluminum chloride (4.9 g, 37 mmol) at 0 oC. The mixture was then warmed to room temperature and stirred for 7 hours. The mixture was poured into ice-water, and was extracted with ethyl acetate and hexane (1:9). The combined organic layers were washed with water and brine, dried (Na2SO4) and concentrated. The residue was purified by flash silica gel chromatography to afford the desired product as a yellowish solid. Yield 40%. $^1$H NMR (500 MHz, CDCl$_3$, δ): 1.28 (d, J=6.8 Hz, 12H), 3.18 (hept, J=6.8 Hz, 2H), 5.34 (br s, 1H), 7.55 (s, 2H), 7.16 (d, d, J=8.6 Hz, 1H), 7.15 (d, J=8.6 Hz, 1H), 7.79 (d, J=8.6 Hz, 1H), 7.81 (d, J=8.6 Hz, 1H); Anal. Calcd for $(C_{19}H_{21}FO_2+H)^+$ and $(C_{19}H_{21}FO_2+H)^+$: 301 and 323. Found: 301 and 323.

EXAMPLE 3

Preparation of 4-(trifluoromethyl)phenyl)-(4-hydroxy-3,5-diisopropylphenyl)methanone (2)

Compound 2 was prepared according to Example 2.
$^1$H NMR (500 MHz, CDCl$_3$, δ): 1.27 (d, J=6.6 Hz, 12H), 3.18 (hept, J=6.6 Hz, 2H), 5.40 (br s. 1H), 7.58 (s, 2H), 7.74 (d, J=8.0 Hz, 2H), 7.85 (d, J=8.0 Hz, 2H); Anal. Calcd for (C$_{20}$H$_{21}$F$_3$O$_2$+H)$^+$ and (C$_{20}$H$_{21}$F$_3$O$_2$+Na)$^+$: 351 and 373. Found: 351 and 373.

EXAMPLE 4

(4-hydroxy-3,5-diisopropylphenyl)-(4-nitrophenyl)methanone (3)

Compound 3 was prepared according to Example 2.
$^1$H NMR (500 MHz, CDCl$_3$, δ): 1.27 (d, J=6.9 Hz, 12H), 3.20 (hept, J=6.9 Hz, 2H), 5.73 (br s. 1H), 7.57 (s, 2H), 7.89 (d, J=8.8 Hz, 2H), 8.33 (d, J=8.8 Hz, 2H); Anal. Calcd for (C$_{19}$H$_{21}$NO$_4$+H)$^+$ and (C$_{19}$H$_{21}$NO$_4$+Na)$^+$: 328 and 350. Found: 328 and 350.

EXAMPLE 5

(3-fluoro-4-(trifluoromethyl)phenyl)-(4-hydroxy-3,5-diisopropylphenyl)methanone (4)

Compound 4 was prepared according to Example 2.
$^1$H NMR (500 MHz, CDCl$_3$, δ): 1.28 (d, J=6.9 Hz, 12H), 3.18 (hept, J=6.9 Hz, 2H), 5.39 (s, 1H), 7.56 (s, 2H), 7.59-7.57 (m, 1H), 7.73 (t, J=8.1 Hz, 1H); Anal. Calcd for C$_{20}$H$_{21}$F$_4$O$_2$ (M+H) 369, found 369.

EXAMPLE 6

(3-(trifluoromethyl)phenyl)-(4-hydroxy-3,5-diisopropylphenyl)methanone (5)

Compound 5 was prepared according to Example 2.
$^1$H NMR (500 MHz, CDCl$_3$, δ): 1.27 (d, J=6.9 Hz, 12H), 3.21 (hept, J=6.6 Hz, 2H), 5.62 (br s. 1H), 7.58 (s, 2H), 7.63 (t, J=7.9 Hz, 1H), 7.83 (d, J=7.9 Hz, 1H), 7.98 (d, J=7.9 Hz, 1H), 8.02 (s, 1H); Anal. Calcd for (C$_{20}$H$_{21}$F$_3$O$_2$+H)$^+$ and (C$_{20}$H$_{21}$F$_3$O$_2$+Na)$^+$: 351 and 373. Found: 351 and 373.

EXAMPLE 7

(3-fluoro-5-(trifluoromethyl)phenyl)-(4-hydroxy-3,5-diisopropylphenyl)methanone (6)

Compound 6 was prepared according to Example 2.
$^1$H NMR (500 MHz, CDCl$_3$, δ): 1.27 (d, J=6.9 Hz, 12H), 3.19 (hept, J=6.9 Hz, 2H), 5.41 (s, 1H), 7.53 (d, J=8.2 Hz, 1H), 7.56 (s, 2H), 7.68 (d, J=8.2 Hz, 1H), 7.80 (s, 1H). Anal. Calcd for C$_{20}$H$_{21}$F$_4$O$_2$ (M+H)$^+$369, found 369.

EXAMPLE 8

(4-hydroxy-3,5-diisopropylphenyl)-(naphthalen-2-yl)methanone (7)

Compound 7 was prepared according to Example 2.
$^1$H NMR (500 MHz, CDCl$_3$, δ): 1.28 (d, J=6.9 Hz, 12H), 3.20 (hept, J=6.9 Hz, 2H), 5.34 (s, 1H), 7.61-7.55 (m, 2H), 7.66 (s, 2H), 8.04-7.75 (m, 4H), 8.26 (s, 1H). Anal. Calcd for C$_{23}$H$_{25}$O$_2$ (M+H)$^+$ 333, found 333.

EXAMPLE 9

(3,5-bis(trifluoromethyl)phenyl)-(4-hydroxy-3,5-diisopropylphenyl)methanone (8)

Compound 8 was prepared according to Example 2.
$^1$H NMR (500 MHz, CDCl$_3$, δ): 1.28 (d, J=6.9 Hz, 12H), 3.19 (hept, J=6.9 Hz, 2H), 5.41(br s. 1H), 7.56 (s, 2H), 8.07 (s, 1H), 8.22 (s, 2H); Anal. Calcd for (C$_{21}$H$_{20}$F$_6$O$_2$+H)$^+$and (C$_{21}$H$_{20}$F$_6$O$_2$+Na)$^+$: 419 and 441. Found: 419 and 441.

EXAMPLE 10

(4-tert-butylphenyl)-(4-hydroxy-3,5-diisopropylphenyl)methanone (9)

Compound 9 was prepared according to Example 2.
$^1$H NMR (500 MHz, CDCl$_3$, δ): 1.28 (d, J=6.9 Hz, 12H), 1.37 (s, 9H), 3.18 (hept, J=6.9 Hz, 2H), 5.30 (br s. 1H), 7.49 (d, J=8.4 Hz, 2H), 7.60 (s, 2H), 7.73 (d, J=8.4 Hz, 2H); Anal. Calcd for (C$_{23}$H$_{30}$O$_2$+H)$^+$ and (C$_{23}$H$_{30}$O$_2$+Na)$^+$: 339 and 361. Found: 339 and 361.

EXAMPLE 11

(4-hydroxy-3,5-diisopropylphenyl)-(4-isobutylphenyl)methanone (10)

Compound 10 was prepared according to Example 2.
$^1$H NMR (500 MHz, CDCl$_3$, δ): 0.89 (t, J=7.4 Hz, 6H), 1.27 (d, J=5.5 Hz, 6H), 1.65 (m, 4H), 2.93 (tq, J=6.9, 6.9 Hz, 2H), 5.34 (br s. 1H), 7.52 (s, 2H), 7.74 (d, J=8.3 Hz, 2H), 7.84 (d, J=8.3 Hz, 2H); Anal. Calcd for (C$_{22}$H$_{25}$F$_3$O$_2$+H)$^+$ and (C$_{22}$H$_{25}$F$_3$O$_2$+Na)$^+$: 379 and 401. Found: 379 and 401.

EXAMPLE 12

(4-hydroxy-3,5-diisopropylphenyl)-(4-iodophenyl)methanone (11)

Compound 11 was prepared according to Example 2.
$^1$H NMR (500 MHz, CDCl$_3$, δ): 1.28 (d, J=6.9 Hz, 12H), 3.17 (hept, J=6.9 Hz, 2H), 5.31 (br s. 1H), 7.49 (d, J=8.3 Hz, 2H), 7.55 (s, 2H), 7.83 (d, J=8.3 Hz, 2H); Anal. Calcd for (C$_{19}$H$_{21}$IO$_2$+H)$^+$ and (C$_{19}$H$_{21}$IO$_2$+Na)$^+$: 409 and 433. Found: 409 and 433.

EXAMPLE 13

(4-hydroxy-3,5-diisopropylphenyl)-(4-methoxyphenyl)methanone (12)

Compound 12 was prepared according to Example 2.
$^1$H NMR (500 MHz, CDCl$_3$, δ): 1.20 (d, J=6.9 Hz, 12H), 2.97 (hept, J=6.9 Hz, 2H), 3.91 (s, 3H), 7.01 (d, J=8.8 Hz, 2H), 7.20 (s, 2H), 8.20 (dd, J=2.2, 6.8 Hz, 2H); Anal. Calcd for (C$_{20}$H$_{24}$O$_3$+H)$^+$: 313. Found: 313.

EXAMPLE 14

(4-cyanophenyl)-(4-hydroxy-3,5-diisopropylphenyl) methanone (13)

Compound 13 was prepared according to Example 2.
$^1$H NMR (500 MHz, CDCl$_3$, δ): 1.27 (d, J=6.8 Hz, 12H), 3.18 (hept, J=6.9 Hz, 2H), 5.40 (br s. 1H), 7.55 (s, 2H), 7.80 (ABq, Δγ=22.2 Hz, J=6.8 Hz, 2H), 7.81 (ABq, Δγ=22.2 Hz, J=6.6 Hz, 2H); Anal. Calcd for $(C_{20}H_{21}NO_2+H)^+$ and $(C_{20}H_{21}NO_2+Na)^+$:308 and 330. Found: 308 and 330.

EXAMPLE 15

(6-(trifluoromethyl)pyridin-3-yl)-(4-hydroxy-3,5-diisopropylphenyl)methanone (14)

CY176 was prepared according to Example 2.
$^1$H NMR (500 MHz, CDCl$_3$, δ): 1.29 (d, J=6.9 Hz, 12H), 3.18 (hept, J=6.9 Hz, 2H), 5.41 (br s. 1H), 7.59 (s, 2H), 7.84 (d, J=7.8 Hz, 1H), 8.24 (dd, J=8.1, 1.7 Hz, 1H), 9.03 (s, 1H); Anal. Calcd for $(C_{19}H_{20}F_3NO_2+H)^+$ and $(C_{19}H_{20}F_3NO_2+Na)^+$: 352 and 374. Found: 352 and 374.

EXAMPLE 16

(4-bromophenyl)-(4-hydroxy-3,5-diisopropylphenyl) methanone (15)

Compound 15 was prepared according to Example 2.
$^1$H NMR (500 MHz, CDCl$_3$, δ): 1.28 (d, J=6.9 Hz, 12H), 3.17 (hept, J=6.9 Hz, 2H), 5.33 (br s. 1H), 7.55 (s, 2H), 7.62 (m, 4H); Anal. Calcd for $(C_{19}H_{21}BrO_2+H)^+$ and $(C_{19}H_{21}BrO_2+Na)^+$: 362 and 364. Found: 363 and 383.

EXAMPLE 17

(4-hydroxy-3,5-diisopropylphenyl)-(4-propylphenyl) methanone (16)

Compound 16 was prepared according to Example 2.
$^1$H NMR (500 MHz, CDCl$_3$, δ): 0.98 (t, J=7.2, 3H), 1.28 (d, J=6.9 Hz, 12H), 1.69 (m, 2H), 2.67 (t, J=7.4, 2H), 3.18 (hept, J=6.9 Hz, 2H), 5.34 (br s. 1H), 7.27 (d, J=8.2 Hz, 2H), 7.59 (s, 2H), 7.71 (d, J=8.2 Hz, 2H); Anal. Calcd for $(C_{22}H_{28}O^2+H)^+$ and $(C_{22}H_{28}O_2+Na)^+$: 325 and 347. Found: 325 and 327.

EXAMPLE 18

(4-chlorophenyl)-(4-hydroxy-3,5-diisopropylphenyl) methanone (17)

Compound 17 was prepared according to Example 2.
$^1$H NMR (500 MHz, CDCl$_3$, δ): 1.28 (d, J=6.9 Hz, 12H), 3.17 (hept, J=6.9 Hz, 2H), 5.31 (br s. 1H), 7.45 (d, J=8.5 Hz, 2H), 7.56 (s, 2H), 7.71 (d, J=8.5 Hz, 2H); Anal. Calcd for $(C_{19}H_{21}ClO_2+H)^+$ and $(C_{19}H_{21}ClO_2+Na)^+$: 317 and 339. Found: 317 and 319.

EXAMPLE 19

Preparation of 4-((4-(trifluoromethyl)phenyl)-(methoxyimino)methyl)-2,6-diisopropylphenol (18)

To a solution of compound 2 (448 mg, 1.28 mmol), as prepared in Example 2, 8 mL of pyridine was added methoxyamine (1.07 g, 12.8 mmol). The reaction mixture was stirred at room temperature for 33 h and concentrated. The residue was purified on silica gel flash column chromatography (hexanes:dichloromethane=3:2) to afford a yellow oil (485 mg, 99.9%). $^1$H NMR (500 MHz, CDCl$_3$, δ): 1.27-1.21 (d, J=6.9 Hz, 12H), 3.20-3.00 (hept, J=6.9 Hz, 2H), 4.00+3.97 (s, 3H), 4.99+4.96 (s, 1H), 7.98-7.06 (m, 6H). Anal. Calcd for $C_{21}H_{23}F_3NO_2$ (M-H)− 378, found 378.

EXAMPLE 20

Preparation of 4-(4-(trifluoromethyl)benzyl)-2,6-diisopropylphenol (19)

To a solution of compound 2 (486 mg, 1.4 mmol), as prepared in Example 2, 12 mL of dichloromethane at 0° C. was added trifluorosulfonic acid (0.6 mL, 5.5 mmol), followed by triethylsilane (0.7 mL, 4.1 mmol). The reaction mixture was stirred at this temperature for 36 h, quenched by saturated aqueous NaHCO$_3$ and extracted by ethyl ether (150 mL). The organic phase was washed by brine and dried over anhydrous MgSO$_4$. After filtration, the solution was concentrated in vacuo. The crude product was purified by silica gel flash column chromatography (toluene:hexanes=1:1) to afford the desired product as a white solid (100 mg, 21.4%). $^1$H NMR (500 MHz, CDCl$_3$, δ): 1.23 (d, J=6.7 Hz, 6H), 1.24 (d, J=6.7 Hz, 6H), 3.13 (hept, J=6.9 Hz, 2H), 3.96 (s, 2H), 4.68 (s, 1H), 6.85 (s, 2H), 7.28 (d, J=8.1 Hz, 2H), 7.52 (d, j=8.1 Hz, 2H); Anal. Calcd for $C_{20}H_{22}F_3O_2$ (M-H) 351, found 351.

EXAMPLE 21

Preparation of 4-((4-(trifluoromethyl)phenyl)(hydroxy)methyl)-2,6-diisopropylphenol (20)

To a solution of compound 2 (308 mg, 0.9 mmol), as prepared in Example 2, reagent grade ethanol was added sodium borohydride (165 mg, 4.4 mmol). The reaction mixture was stirred for 11 h at room temperature, quenched by 1 N HCl and extracted by ethyl ether. The organic phase was washed by saturated aqueous NaHCO$_3$ and brine and dried over anhydrous MgSO$_4$. After filtration, the solution was condensed by rotavapor. The crude product was purified by silica gel flash column chromatography (hexanes:dichloromethane=1:2) to afford a white solid (100 mg, 33.8%). $^1$H NMR (500 MHz, CDCl$_3$, δ): 1.25 (d, J=6.9 Hz, 12H), 3.13 (hept, J=6.9 Hz, 2H), 4.81 (s, 1H), 5.82 (s, 1H), 7.02 (s, 2H), 7.51 (d, J=8.1 Hz, 2H), 7.58 (d, J=8.1 Hz, 2H); Anal. Calcd for $C_{20}H_{22}F_3O$ (M-H)− 335, found 335.

EXAMPLE 22

Preparation of 4-hydroxy-3,5-diisopropylphenyl-(4-(methylsulfonyl)phenyl)methanone (21)

To a solution of 4-methylsulfonylbenzoic acid (4.08 g, 24 mmol) and oxalyl chloride (3.9 mL, 44 mmol) in DCM (70 mL), three drops of DMF was added at 0° C. The reaction mixture was stirred at room temperature for 3 hours and concentrated on a rotavapor. The residue was dissolved in 20 mL of DCM and was added into a suspension of 2,6-diisopropylphenol (2.12 g, 11.9 mmol) and aluminum chloride (1.6 g, 12 mmol in 50 mL of DCM. After stirring for 14 hour, the reaction mixture was poured into 100 mL of ice-water and extracted with diisopropyl ether (2×100 mL). The organic layer was washed with 1 N HCl, saturated aqueous NaHCO$_3$, and brine, and was dried over anhydrous MgSO$_4$. After filtration, the solution was condensed on a rotary evaporator. The crude product was suspended in 100 mL of methanol and 30 mL of water. The resultant suspension was treated with an excess amount of solid NaOH for 16 h at room temperature and acidified by 1 N HCl to pH of 4. The reaction mixture was extracted with ethyl acetate (2×100 mL). After washing with saturated aqueous NaHCO$_3$ and brine, the organic layer was dried over anhydrous Na$_2$SO$_4$ and filtered. The solution was concentrated and the residue was purified by flash silica gel chromatography to afford the desired product as a yellow solid (550 mg, Yield 13%). $^1$H NMR (500 MHz, CDCl$_3$, δ): 1.27 (s, 6H), 1.29 (s, 6H), 3.12 (s, 3H), 3.18 (hept, J=6.9 Hz, 2H), 5.40 (br s, 1H), 7.57 (s, 2H), 7.90 (dd, J=6.6, 1.7 Hz, 2H), 8.06 (dd, J=6.5, 1.7 Hz, 2H); Anal. Calcd for (C$_{19}$H$_{21}$FO$_2$+H)$^+$: 361. Found: 361.

EXAMPLE 23

Rapid Tissue Penetration by 2,6-diisopropyl phenol Demonstrated by PK Analysis

Three rats were administered 2,6-diisopropyl phenol dissolved in DMSO at 5 mg/kg intravenously. Blood was drawn and processed to plasma for 2,6-diisopropyl phenol quantitation at 1, 3, 5, 10, 30, 60, 120, and 240 min post administration. Plasma 2,6-diisopropyl phenol was quantitated using a validated GC/MS assay. Time plasma concentration curve was processed using a two compartment PK model supported by WinNonlin. The PK parameters are shown in Table 1.

TABLE 1

| PK parameters for 2,6-diisopropyl phenol: | |
|---|---|
| AUC | 0.4 h*g/ml |
| C$_{max}$ | 0.3 g/ml |
| V1 | 15 L/kg |
| V2 | 58 L/kg |
| Vss | 73 L/kg |
| CL | 12 L/h/kg |

2,6-diisopropyl phenol PK is characterized by large volume of distribution and rapid clearance indicative of its ability to penetrated peripheral tissues rapidly.

EXAMPLE 24

High Brain Penetration Ability of 2,6-diisopropyl phenol as Demonstrated by PK/PD Analysis 2,6-diisopropyl phenol dissolved in DMSO and administered to rat put the rat to sleep for 20 min, at which time the plasma 2,6-diisopropyl phenol concentration was calculated to be 0.75 μM using the PK data in example 23. Brain concentration of 2,6-diisopropyl phenol should be equivalent to the IC$_{50}$ of 2,6-diisopropyl phenol binding to its effector (GABA Cl channel). This was determined to be 96 μM using a competitive radioligand binding assay with GABA receptor and radiolabeled [$^3$H]TBOB. The data demonstrated that 2,6-diisopropyl phenol has a high intrinsic affinity for the brain and the brain was able to accumulated 2,6-diisopropyl phenol to a level 6-fold higher than that of plasma. This is consistent with the highly penetrant nature of 2,6-diisopropyl phenol as demonstrated by PK analysis.

EXAMPLE 25

2,6-diisopropyl phenol Antioxidant Activity 2,6-diisopropyl phenol and 2,6-diisopropyl phenol analogs were tested for antioxidant activity using the Total Antioxidant Status Assay kit from CalBiochem (San Diego, Calif.). The assay used relies on the ability of antioxidants in the sample to inhibit the oxidation of ABTS (2,2'-Azino-di-[3-ethylbenzthiazoline sulphonate]) to ABTS+ by metmyoglobin (a peroxidase). The amount of ABTS+ produced was monitored at 600 nm. Under the reaction conditions used, the antioxidants in the sample suppress the absorbance at 600 nm to a degree which is proportional to their concentration and antioxidant activity. The IC$_{50}$ was defined at the concentration at which 50% suppression occurred.

TABLE 2

| Drug ID | Antioxidant activity |
|---|---|
| 2,6-diisopropyl phenol | <10$^{-5}$M |
| 20 | 2.8 × 10$^{-5}$M |
| 1 | >10$^{-3}$M |
| 2 | >10$^{-3}$M |
| 3 | >10$^{-3}$M |
| 4 | >10$^{-3}$M |
| 5 | >10$^{-3}$M |
| 6 | >10$^{-3}$M |
| 9 | >10$^{-3}$M |
| 11 | >10$^{-3}$M |
| 22 | >10$^{-3}$M |
| 13 | >10$^{-3}$M |
| 14 | >10$^{-3}$M |

EXAMPLE 26

This example demonstrates the preparation of a pharmaceutical composition comprising 2,6-diisopropyl phenol, albumin, vitamin E-TPGS, and 1% oil.

An emulsion containing 2% (by weight) of 2,6-diisopropyl phenol was prepared by the following method. The aqueous phase was prepared by adding glycerol (2.25% by weight) and human serum albumin (0.5% by weight) into water for injection and stirred until dissolved. The aqueous phase was passed through a filter (0.2 μm filter). Surfactant, e.g., Vitamin E-TPGS (1%), was added to aqueous phase. The oil phase consisted of 2,6-diisopropyl phenol (2% by weight of emulsion), soybean oil (1% by weight of emulsion) and lecithin (0.4% by weight of emulsion). The oil phase was added to the aqueous phase and homogenized at 10,000 RPM for 5 min. The crude emulsion was high pressure homogenized at 20,000 psi and recirculated for 8-15 cycles at 5° C. Alternatively, discrete passes through the homogenizer were used. The final emulsion was filtered (0.2 μm filter) and stored under nitrogen.

The resulting pharmaceutical composition contained the following general ranges of components (weight %): 2,6-diisopropyl phenol 0.5-5%; human serum albumin 0.01-3%; Vitamin E-TPGS 0.1-2%; lecithin (0.05-1%), soybean or other oil (0.1%-5%); glycerol 2.25%; water for injection q.s. to 100; pH 5-8. Deferoxamine was optionally added (0.001%-0.1% by weight).

EXAMPLE 27

Specific Binding of 2,6-diisopropyl phenol to the GABA$_A$ Chloride Channel

GABA$_A$ receptors are heteropentameric membrane proteins of 1 alpha subunit, 1 beta subunit, and 1 gamma subunit. These subunits form the chloride channel and control neuronal membrane potential by regulating chloride flux across cell membrane. The 2,6-diisopropyl phenol binding site on GABA$_A$ was defined using a series of competitive binding assays.

Frozen bovine hippocampus was thawed and homogenized in 40 volumes of ice-cold 0.32 M sucrose. The suspension was centrifuged at 1000×g for 10 minutes at 4° C. The pellet was washed twice in assay buffer and reacted with radioactive ligand in presence or absence of 2,6-diisopropyl phenol at 10 −4 M final concentration. The amount of radioactivity remained on the Whatman filter following filtration of the reaction mix and two washes with assay buffer was determined using a liquid scintillation counter. Inhibition of radioactive ligand binding by 2,6-diisopropyl phenol represents the competitive binding of 2,6-diisopropyl phenol to the same site as the radioactive ligand. GABA$_A$ agonist site, GABA$_A$ alpha-1 site, GABA$_A$ alpha-5 site, GABA$_A$ alpha-6 site, and GABA$_A$ Cl channel were assayed using 3H-GABA, 3H-Flunitrazepam, 3H-RY80, 3H-Ro 15-4513, and 3H-TBOB.

Figure 1B:
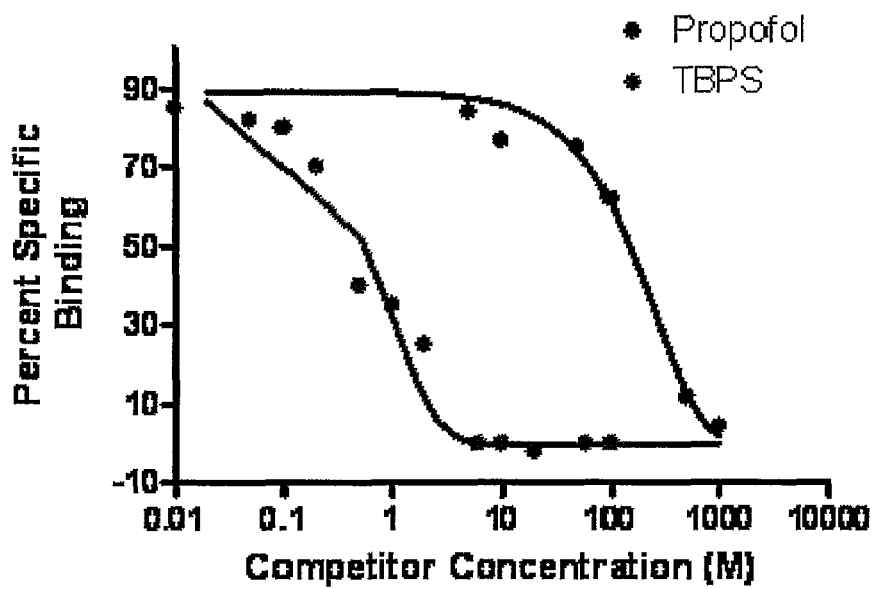
FIG. 1B is a plot depicting the inhibition of TBOB binding to $GABA_A$ (Percent Specific Binding) in the presence of increasing concentrations ($10^{-2}$, $10^{-1}$, $10^0$, 10, $10^2$, $10^3$, and $10^4$ M) of propofol as compared to TBPS.

To determine the binding constant (KD) of 2,6-diisopropyl phenol for these sites, binding was determined in presence of increasing concentration of 2,6-diisopropyl phenol and the KD determined graphically. 2,6-diisopropyl phenol at 10-4M only inhibited the binding of TBOB to the chloride channel of the GABA$_A$ receptor. No significant inhibition of the agonist site, the alpha 1 site, the alpha 2 site, or the alpha 6 site was observed. This is shown in FIG. 1A. The inhibition of TBOB binding to GABA$_A$ receptor in the presence of increasing concentrations of 2,6-diisopropyl phenol or TBPS (a TBOB analog) gave the binding constants of 5.74×10 −6 M and 3.10 10 −8 M, respectively, as shown in FIG. 1B.

EXAMPLE 28

Compound 2 and Compound 11 Exhibit Enhanced GABA$_A$ Binding In Vitro and Enhanced Anesthetic Activity in vivo A series of 2,6-diisopropyl phenol analogs were prepared and their in vivo anesthetic activity and in vitro GABA$_A$ binding activity determined.

Drugs solubilized in DMSO were administered to rats by tail vein injection (N=5 rats per group). A dose level of 28 μmol/kg (5 mg/kg for 2,6-diisopropyl phenol) was used to compensate for differences in molecular weight of the analogs. Anesthetic activity in vivo was determined as time to recovery of righting reflex following administration of the compounds. GABA$_A$ binding activity in vitro was performed as described in Example 27.

Figure 2A:
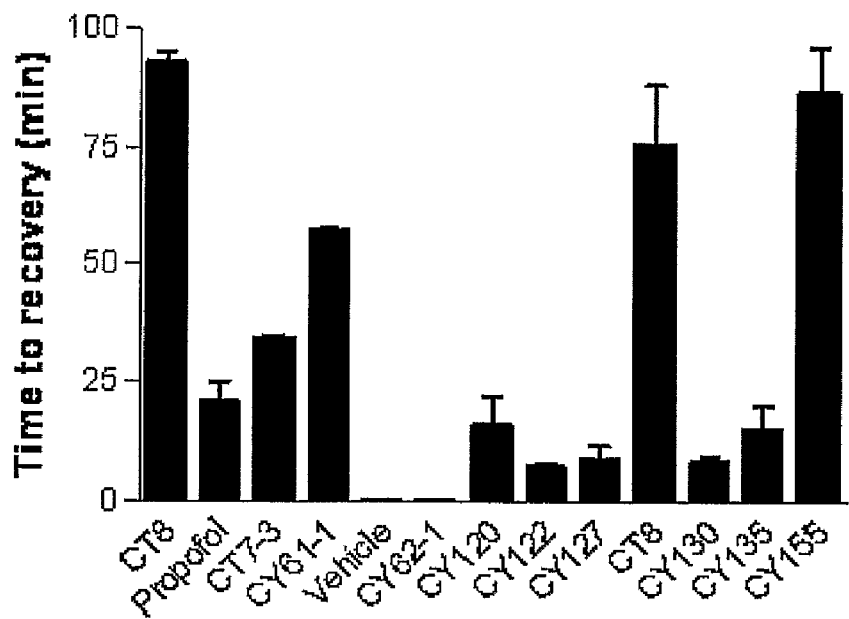
FIG. 2A is a bar chart depicting anaesthetic effect in terms of time to recovery (min.) for propofol as compared to CT8(2 samples), CT7-3, CY6-1-1, CY62-1, CY120, CY122, CY127, CY130, CY135, and CY155, and further compared to a vehicle-only control.
Figure 2B:
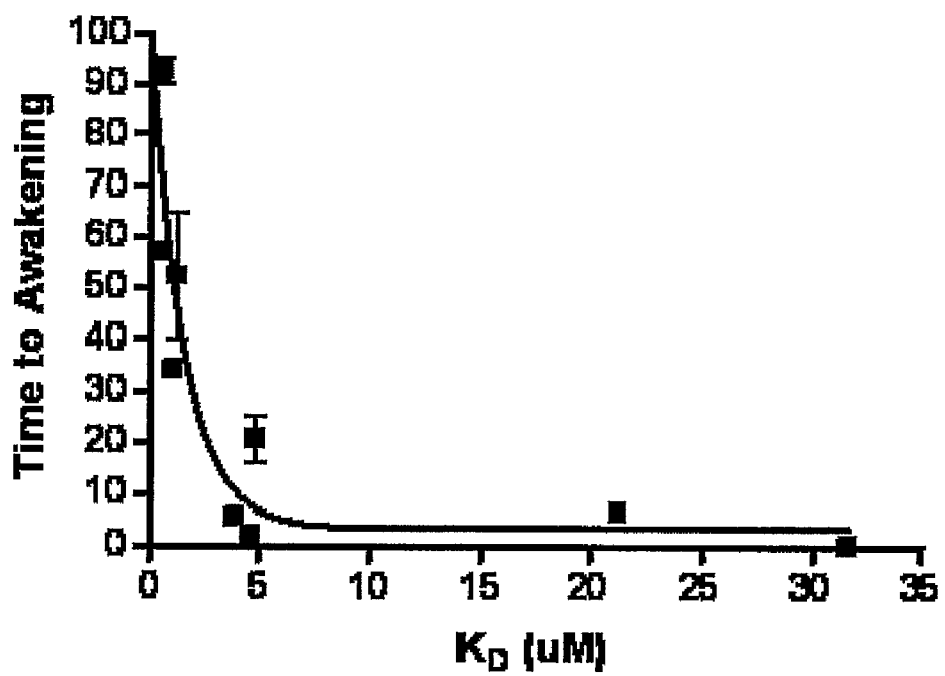
FIG. 2B is a plot depicting the correlation between affinity to $GABA_A$ receptor ($K_D$) in vitro and anaesthetic activity in vivo (Time to Awakening (min.)).

2,6-diisopropyl phenol at 5 mg/kg (28 mmol/kg) anesthetized rats for 20 min. Compound 2 and compound 11 at equivalent dose anesthetized the rats for 75-92 min and 86 min, respectively. Compound 2 and compound 11 did not have toxicity above that of 2,6-diisopropyl phenol at equimolar dose. There was a good correlation between affinity to GABA$_A$ receptor in vitro and anesthetic activity in vivo (See FIG. 2B). Compound 2 and compound 11 exhibited the KD of 0.42×10 −6 M and 0.36×10 −6 M respectively, >10-fold lower than that for 2,6-diisopropyl phenol (5.74×10 −6 M). Compound 2 and compound 11 exhibited the most potent anesthetic activity in vivo (See FIG. 2A). From these results, it appears that compound 2 may be a safer agent for inhibition of GABA$_A$ receptor to treat stroke or neurodegenerative diseases involving GABA$_A$ receptor than 2,6-diisopropyl phenol and could provide improved neuroprotective activity during stroke and other neurodegenerative diseases where GABA$_A$ receptor is involved.

EXAMPLE 29

Improved Therapeutic Index of Compound 2

Figure 3A:
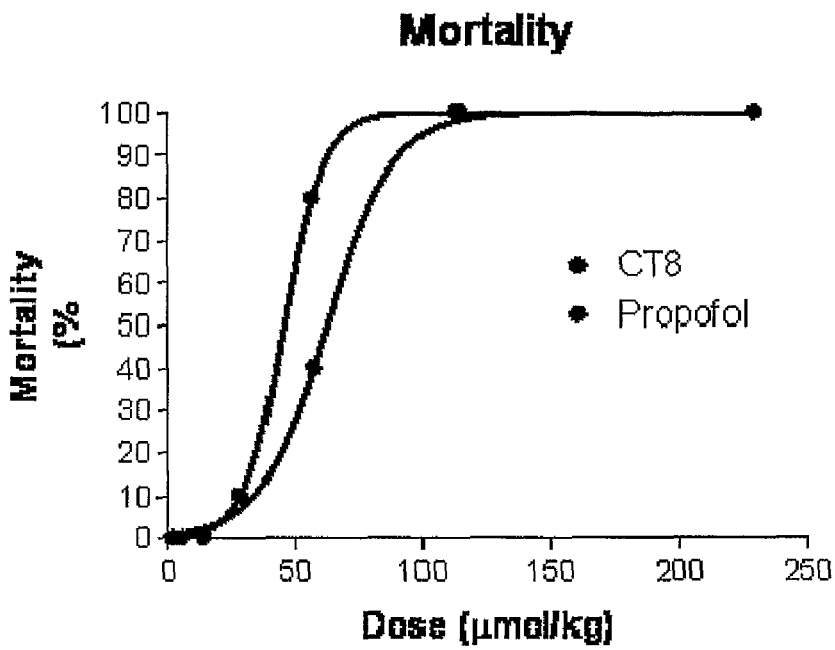
FIG. 3A is a plot depicting mortality (%) by dose (μM/kg) of CT8 as compared to propofol.
Figure 3B:
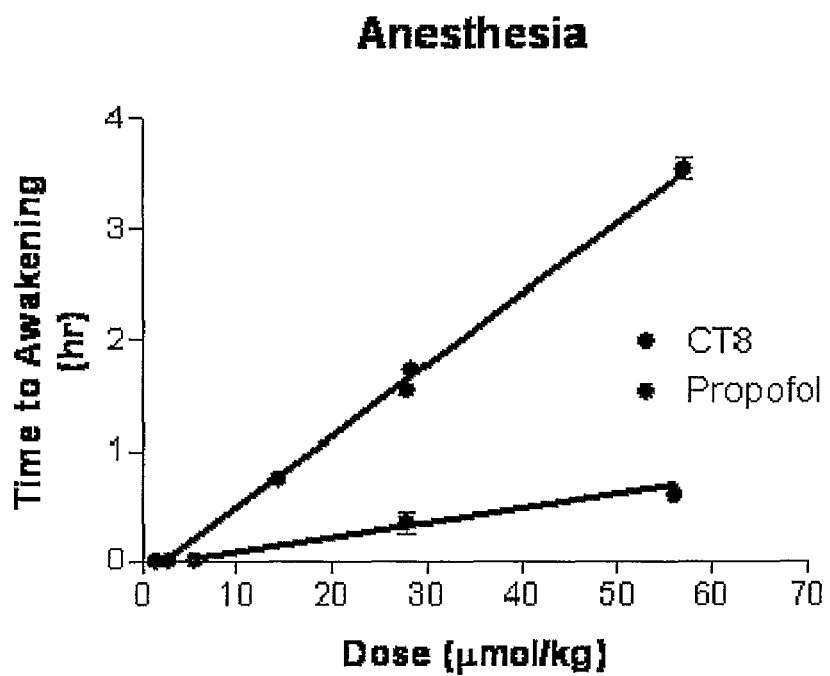
FIG. 3B is a plot depicting time to awakening (hours) by dose (μM/kg) of CT8 as compared to propofol.

To explore the potential clinical application of compound 2, its therapeutic index was compared to that of 2,6-diisopropyl phenol. A dose escalation experiment was performed in rats in order to compare the toxicity and the pharmacodynamic of compound 2 against 2,6-diisopropyl phenol. Drugs solubilized in DMSO were administered to rats (5 rats per group). Anesthetic activity in vivo was determined as time to recovery of righting reflex. Mortality was also monitored and the LD50 curves for 2,6-diisopropyl phenol and compound 2 were constructed. In order to adjust for the differences in molecular weight between the two compounds, umol/kg dose was used. Compound 2 exhibited the same toxicity profile as 2,6-diisopropyl phenol with a calculated LD10 of 29 μmol/kg in comparison to the calculated LD10 of 28 μmol/kg for 2,6-diisopropyl phenol. There was a linear dose response for anesthetic activity for both compound 2 and 2,6-diisopropyl phenol. However, compound 2 exhibited higher anesthetic activity in vivo than 2,6-diisopropyl phenol. At LD10, the rats were asleep for 1.73 hr when treated with compound 2 and only 0.35 hr when treated with 2,6-diisopropyl phenol. Mortality curves were constructed for 2,6-diisopropyl phenol and compound 2 (See FIG. 3A). The LD50 and LD10 were calculated to be 45.3 μmol/kg and 28 μmol/kg for 2,6-diisopropyl phenol and 62.1 μmol/kg and 29 μmol/kg for compound 2. Anesthesia response curves show that Compound 2 exhibited better anesthetic activity than 2,6-diisopropyl phenol at all dose levels (See FIG. 3B). At LD10, the rats were asleep for 0.35 hr for 2,6-diisopropyl phenol versus 1.73 hr for compound 2. These results show that compound 2 may be a safer agent for inhibition of GABA$_A$ receptor to treat stroke or neurodegenerative diseases involving GABA$_A$ receptor than 2,6-diisopropyl phenol. The longer sleeping time associated with compound 2 and other potentially disclosed analogs compared to 2,6-diisopropyl phenol make them also useful in prolonged sedation or as sleeping aids.

EXAMPLE 30

PK of Compound 2 Exhibited Delayed Clearance and Small Volume Distribution at Steady Stateversus 2,6-diisopropyl phenol Compound 2 and 2,6-diisopropyl phenol were solubilized in DMSO. Rats (N=3 per group) were dosed with either compound 2 or 2,6-diisopropyl phenol intravenously via the jugular vein cannula and blood samples (200 μl) taken via the common carotid cannula at 1, 3, 5, 10, 30, 60, 120, and 240 minutes post Test Material administration. Compound 2 and 2,6-diisopropyl phenol in the blood samples were quantitated using GC/MS and two compartmental PK analysis performed using WinNonlin.

As shown in Table 3, compound 2 exhibited higher AUC, Cmax, and lower volume distribution at steady state (Vss), volume of the central compartment (Vc), volume of the tissue compartment (Vt), and CL than 2,6-diisopropyl phenol. The longer residence time of compound 2 would be beneficial in therapeutic application of compound 2 as it would allow for more once daily or more infrequent dosing than the current continuous infusion of propfol in the treatment of stroke or neurodegenerative diseases involving the GABA receptor. The more favorable pharmacokinetics of compound 2 and other potentially disclosed analogs compared to 2,6-diisopropyl phenol make them also useful in prolonged sedation or as sleeping aids.

TABLE 3

|  | AUC (hr * ug/ml) | Cmax (ug/ml) | Vc (L/kg) | CL (L/hr/kg) | Vss (L/kg) | Vt (L/kg) |
|---|---|---|---|---|---|---|
| Compound 2 | 127 | 283 | 0.04 | 0.08 | 5.3 | 5.2 |
| 2,6-diisopropyl phenol | 0.4 | 0.3 | 15.0 | 11.7 | 73.0 | 58.0 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating or ischemic injury in a human, wherein the method comprises administering to the human an amount of a 2,6-diisopropyl phenol analog selected from the group consisting of: (4-fluorophenyl)-(4-hydroxy-3,5-diisopropylphenyl)methanone, (4-(trifluoromethyl)phenyl)-(4-hydroxy-3,5-diisopropylphenyl)methanone, (4-3,5diisopropylphenyl(4-nitrophenyl)methanone, (3-fluoro-4-(trifluoromethyl) phenyl)-(4-hydroxy-3,5-diiso propylphenyl) methanone, (3-(trifluoromethyl)phenyl)-(4-hydroxy-3,5-diisopropylphenyl)methanone, (3-fluoro-5-(trifluoromethyl) phenyl)-4-hydroxy-3,5-diisopropylphenyl)methanone, (4-hydroxy-3,5-diisopropylphenyl)naphthalene-2-yl)methanone, (3,5-bis(trifluoromethyl)phenyl)-(4-hydroxy-3,5-diisopropylphenyl)methanone, (4-tert-butylphenyl)-(4-hydroxy-3,5-diisopropylphenyl)methanone, (4-hydroxy-3,5-diisopropylphenyl)-(4-isobutylphenyl)methanone, (4-hydroxy-3,5-diisopropylphenyl)-(4-iodophenyl)methanone, (4-hydroxy-3,5-diisopropylphenyl)-(4-methoxyphenyl)methanone, (4-cyanophenyl)-4-hydroxy-3,5-diisopropylphenyl)methanone, (6-(trifluoromethyl)pyridin-3-yl)-(4-hydroxy-3,5-diisopropylphenyl)methanone, (4-bromophenyl)-(4-hydroxy-3,5-diisopropylphenyl)methanone, (4-hydroxy-3,5-diisopropylphenyl)-(4-propylphenyl) methanone, (4-chlorophenyl)-(4-hydroxy-3,5-diisopropylphenyl)methanone, 4-((4-(trifluoromethyl)phenyl)-(methoxyimino)methyl)-2,6-diisopropylphenyl, 4-(4-(trifluoromethyl)benzyl)-2,6-diisopropylphenyl, 4-((4-(trifluoromethyl)phenyl)-(hydroxy)methyl)-2,6-diisopropylphenyl, 4-hydroxy-3,5-diisopropylphenyl)-(4-(methylsulfonyl)phenyl)methanone, and combinations thereof.

2. The method of claim 1 wherein the 2,6-diisopropyl phenol analog is included in a pharmaceutical composition.

3. The method of claim 2, wherein the 2,6-diisopropyl phenol analog is administered by a method selected from the group consisting of oral administration, nasal respiratory administration, aerosol administration, bolus injection, intravenous administration, continuous infusion, intra-arterial administration, rectal administration, vaginal administration, sublingual administration, parenteral administration and cutaneous administration.

4. The method of claim 3, wherein the pharmaceutical composition is for parenteral administration.

5. The method of claim 2, wherein the pharmaceutical composition comprises nanoparticles of the 2,6-diisopropyl phenol analog.

6. The method of claim 5, wherein the pharmaceutical composition is for parenteral administration.

7. The method of claim 2, wherein the pharmaceutical composition comprises a pharmaceutically acceptable carrier.

8. The method of claim 1, wherein the ischemic injury is induced by stroke, hemorrhage or trauma.

9. The method of claim 1, wherein the 2,6-diisopropyl phenol analog is 4-(trifluoromethyl)phenyl)-(4-hydroxy-3,5-diisopropylphenyl)methanone.

10. The method of claim 9, wherein the composition is administered continuously.

11. The method of claim 9, wherein the composition is administered one or more times a day.

12. A method of treating or ischemic injury in a human with a pharmaceutical composition comprising:
 a) 0.5-5 wt % 2,6-diisopropyl phenol or an analog thereof, and
 b) 0.1-5 wt % oil,
 wherein, the composition is administered to a human in an amount effective to treat ischemia.

13. The method of claim 12, wherein the composition further comprises 0.1 to 3 wt % human serum albumin.

14. The method of claim 12, wherein the composition further comprises 0.05 to 1 wt % lecithin.

15. The method of claim 12, wherein the composition further comprises 0.1 to 2 wt % vitamin E-TPGS.

16. The method of claim 12, wherein the composition further comprises about 2.25% glycerol.

17. The method of claim 12, wherein the pharmaceutical composition has a pH of about 5 to about 8.

18. A method for treating ischemia in a human comprising administering to a human a low oil composition comprising 2,6-diisopropyl phenol or an analog thereof in an amount effective to treat ischemia.

19. The method of claim 18, wherein the composition contains less than 5 wt % oil.

20. The method of claim 19, wherein the composition contains less than 3 wt % oil.

21. The method of claim 20, wherein the 2,6-diisopropyl phenol analog is 4-(trifluoromethyl)phenyl)-(4-hydroxy-3,5-diisopropylphenyl)methanone.

22. The method of claim 19, wherein the analog is selected from the group consisting of:
- (4-fluorophenyl)-(4-hydroxy-3,5-diisopropylphenyl) methanone,
- (4-(trifluoromethyl)phenyl)-(4-hydroxy-3,5-diisopropylphenyl)methanone,
- (4-hydroxy-3,5-diisopropylphenyl)-(4-nitrophenyl) methanone,
- (3-fluoro-4-(trifluoromethyl)phenyl)-(4-hydroxy-3,5-diisopropylphenyl)methanone,
- (3-(trifluoromethyl)phenyl)-(4-hydroxy-3,5-diisopropylphenyl)methanone,
- (3-fluoro-5-(trifluoromethyl)phenyl)-(4-hydroxy-3,5-diisopropylphenyl)methanone,
- (4-hydroxy-3,5-diisopropylphenyl)-(naphthalen-2-yl) methanone,
- (3,5-bis(trifluoromethyl)phenyl)-(4-hydroxy-3,5-diisopropylphenyl)methanone,
- (4-tert-butylphenyl)-(4-hydroxy-3,5-diisopropylphenyl) methanone,
- (4-hydroxy-3,5-diisopropylphenyl)-(4-isobutylphenyl) methanone,
- (4-hydroxy-3,5-diisopropylphenyl)-(4-iodophenyl) methanone,
- (4-hydroxy-3,5-diisopropylphenyl)-(4-methoxyphenyl) methanone,
- (4-cyanophenyl)-(4-hydroxy-3,5-diisopropylphenyl) methanone,
- (6-(trifluoromethyl)pyridin-3-yl)-(4-hydroxy-3,5-diisopropylphenyl)methanone,
- (4-bromophenyl)-(4-hydroxy-3,5-diisopropylphenyl) methanone,
- (4-hydroxy-3,5-diisopropylphenyl)-(4-propylphenyl) methanone,
- (4-chlorophenyl)-(4-hydroxy-3,5-diisopropylphenyl) methanone,
- 4-((4-(trifluoromethyl)phenyl)-(methoxyimino)methyl)-2,6-diisopropylphenol,
- 4-(4-(trifluoromethyl)benzyl)-2,6-diisopropylphenol,
- 4-((4-(trifluoromethyl)phenyl)-(hydroxy)methyl)-2,6-diisopropylphenol,
- 4-hydroxy-3,5-diisopropylphenyl)-(4-(methylsulfonyl) phenyl)methanone, and combinations thereof.

23. The method of claim 18, wherein the composition contains less than 2 wt % oil.

* * * * *